United States Patent [19]
Nakajima et al.

[11] 3,937,669
[45] Feb. 10, 1976

[54] CATALYST FOR METHYLATION OF PHENOLS

[75] Inventors: Hitoshi Nakajima, Ageo; Fujio Nomura; Shinichi Izawa, both of Tokyo, all of Japan

[73] Assignee: Asahi Kasei Kogyo Kabushiki Kaisha, Osaka, Japan

[22] Filed: June 10, 1974

[21] Appl. No.: 478,002

Related U.S. Application Data

[62] Division of Ser. No. 207,546, Dec. 13, 1971, Pat. No. 3,855,318.

[30] Foreign Application Priority Data

Dec. 11, 1970  Japan............................. 45-109385
Dec. 17, 1970  Japan............................. 45-112490
Dec. 17, 1970  Japan............................. 45-112491

[52] U.S. Cl................ 252/432; 252/466 J; 252/471; 252/472; 252/473

[51] Int. Cl.$^2$. B01J 21/02; B01J 23/84; B01J 23/78
[58] Field of Search......... 252/432, 466 J, 471, 472, 252/473; 260/620, 621 R, 624 C

[56] References Cited
UNITED STATES PATENTS 3,562,185    2/1971    Friedrichsen et al........... 252/472 X

*Primary Examiner*—W. J. Shine
*Attorney, Agent, or Firm*—Cooper, Dunham, Clark, Griffin & Moran

[57] ABSTRACT

Vapor phase methylation of phenols with methanol in contact with a vanadium oxide catalyst which may additionally contain iron oxide and at least one other oxide of magnesium, titanium, manganese, beryllium or boron.

5 Claims, No Drawings

CATALYST FOR METHYLATION OF PHENOLS

This is a division of application Ser. No. 207,546 filed Dec. 13, 1971, now U.S. Pat. No. 3,855,318.

BACKGROUND OF INVENTION

This invention relates to a catalytic process for the methylation of the ortho position of phenols having at least one ortho hydrogen and to certain novel catalysts useful in the process.

Compounds such as those represented by the general formula:

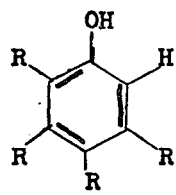

are of known utility. They are especially useful in the preparation of polymers such as polyphenylene oxide. In the formula each R is a monovalent substituent selected from the group consisting of hydrogen, methyl, phenyl, and methyl substituted phenyl.

Methods are already available for the alkylation of phenols in the ortho position. They are described, for example, in British Pat. Nos. 717,588 and 1,112,914; U.S. Pat. No. 3,446,856; Japanese Pat. Publications 27367/1964 and 29293/1970; and in the report by Enomoto et al. in the Catalyst Research Conference of 1968.

British Pat. No. 717,588 relates to an alkylation process in which a metal oxide having dehydrating action such as the oxides of aluminum, thorium, zirconium, zinc, iron, manganese, magnesium or calcium are employed as catalysts. The process is not completely satisfactory, however, because it is not sufficiently selective. For example, the methyla- of phenol leads not only to the desired ortho-substituted products but also to undesirably large amounts of the meta and para isomers. The separation of the undesired byproducts is complicated and expensive, but they must be separated especially if the desired product, 2,6-xylenol is to be used for the production of polyphenylene oxide.

U.S. Pat. No. 3,446,856 describes the alkylation reaction using magnesia as a catalyst. This is a somewhat improved procedure, but the elevated temperature, e.g. 475°C. at which it is carried out leads to excessive decomposition of starting materials such as phenol and methanol.

British Patent No. 1,112,914, Enotmoto's method, and the above identified Japanese Patent Publications all relate to improved processes in which the magnesia is enriched with a second or third element. With relatively inexpensive additives there is still appreciable decomposition of the starting materials which is often accompanied by a marked decrease in the activity of the catalyst. The addition of rare earth metals or of uranium or palladium is helpful, but it is also expensive.

Despite extensive research no completely satisfactory method has yet been found for the ortho-methylation of phenols.

THE INVENTION

It has now been discovered in accordance with this invention that phenols can be methylated in the ortho position with methanol using a vanadium oxide catalyst in a vapor phase reaction at elevated temperature. The use of vanadium oxide results in methylation almost exclusively at the ortho position. Moreover, there is reduced decomposition of methanol and increased catalyst life. The use of iron oxide in association with the vanadium oxide leads to improved results. The addition of an oxide of magnesium, titanium, manganese, beryllium, boron, or mixtures of these oxides to produce a polymetallic catalyst results in even greater improvements. These polymetallic catalysts are novel and are specifically included within the scope of this invention.

A further feature of the invention is the discovery that the addition of water vapor to the reaction system in the amount of from about 2 to 12 mols per mol of the phenol utilized helps to prevent the catalysts from breaking down into finer particles or powders which clog the reactor. Thus the life of the catalyst is extended, and the periods between shutdowns of the operation to clean the reactor are prolonged.

The term "oxide" as used in association with various metals in describing and claiming this invention refers to all of the several oxides of the metal known to exist such as $V_2O_5$, $V_2O_4$, $V_2O_3$, $VO$, $Fe_2O_3$, $Fe_3O_4$, $FeO$, $MgO$, $TiO_2$, $MnO_2$, $MnO$, $Mn_3O_4$ and to mixtures of these various oxides.

In the bimetallic vanadium-iron catalysts used in this invention the atomic ratio of iron to vanadium is normally from about 9 to 1/9. The preferred range for optimum results in from 4 to ¼. When at least one compound selected from the group consists of oxides of manganese, magnesium, titanium, beryllium and boron is added, the atomic ratio of vanadium to iron to other metal or mixture of metals is from about 1/9–9 : 1 : 1 – 0.01. The preferred range in polymetallic catalysts is ¼ – 4 : 1 : 1 – 0.1. Preferred catalysts contain oxides of vanadium, iron, magnesium, titanium, and manganese in the defined ratios.

Vanadium and any of the other metals used in the present invention may be obtained from any of their usual compounds such as nitrates, hydroxides, carbonates, oxalates, halides, and the like. They may be converted to the desired oxides by immersing, mixing, coprecipitation or other conventional methods. The methods for preparing the catalysts are illustrated in the examples. In actual use they may be supported on suitable carriers such as alumina, silica, silica-alumina, and the like.

In accordance with the process of the invention a mixture of methanol and the selected phenol is contacted with the catalyst in the vapor phase at an elevated temperature to methylate the phenol at one or both of the ortho positions. A mixture of methanol and phenol, for example, can be converted predominantly to ortho cresol or to 2,6-xylenol, or to a mixture of these compounds.

Phenols which may be methylated by the process of this invention include, for example, phenol itself, 0-cresol, m-cresol, p-cresol, 2,3-xylenol, 2,4-xylenol, 2,5-xylenol, 3,5-xylenol, 2,3,4-trimethylphenol, 2,3,5-trimethylphenol, 3,4,5-trimethylphenol, 2,3,4,5-tetramethylphenol, 0-phenylphenol, p-phenylphenol, 2-tolylphenol, 2,4-diphenylphenol, 2,3-diphenylphenol, 2-xylylphenol, 2-mesitylphenol, 2-durylphenol, 2-phenyl-4-methylphenol, 2-tolyl-4-phenylphenol, 2-phenyl-4-tolylphenol or 3-methyl-5-phenylphenol. All of these phenols may be represented by the formula

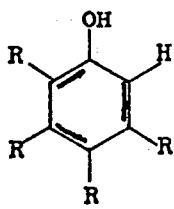

wherein each R is a nonvalent substituent selected from the group consisting of hydrogen, methyl, phenyl, and methyl substituted phenyl.

Any one or a mixture of the above phenols is vaporized together with methanol and passed through a reactor containing the selected catalyst. The reactor may take any of the usual forms such as stationary bed, moving bed, fluidized bed, and the like. The reaction temperature is typically in the range of from about 250°C. to 450°C., with the preferred range being from 300°C. to 400°C. At temperatures appreciably lower than 250°C. there is a noticeable decrease in yield, and as the temperature increases much above 500°C. there is an appreciable increase in the amount of byproducts produced, especially byproducts which are methylated in positions other than the ortho position. There is also a noticeable increase in decomposition of methanol.

A particular advantage of the process of this invention is that it can be carried out at a relatively low temperature compared to known methods so that the cost of operation is decreased. Additionally there is less decomposition of starting materials or products, and the catalyst life is markedly increased.

While some methylation is effected even with small amounts of methanol, it is preferred that there be at least one molar equivalent of methanol for each unsubstituted ortho position in the phenol to be methylated. Normally the molar ratio of methanol to phenol type reactant is from about 1:1 to 10:1. There is little advantage to increasing the molar ratio appreciably above 10:1 since the charge in yield does not compensate for the additional cost.

The presence of a reaction inert gas such as nitrogen, hydrogen, carbon monoxide, carbon dioxide or methane is often helpful. As mentioned above the use of water vapor helps to extend the life of the catalyst even longer than usual. When used, it may be employed in a water vapor-phenol reactant mole ratio of from about 2:1 to 12:1. When the amount of water vapor is lower than about 2 mols per mol of phenol the effect on extending catalyst life is decreased. On the other hand, when the ratio increased appreciably above 12:1 the partial pressure of the phenol decreases and this in turn reduces the space-time yield of methylated products.

The reaction pressure is not critical. It may be carried out at atmospheric pressure, and may also be carried out over a wide range of pressure varying from about 0.5 to 50 atmospheres.

Best catalytic activity and optimum selectivity is achieved by maintaining the gas space velocity at from about 360 to 18,000 hr$^{-1}$. The preferred range from the viewpoint of economical operation is 900 to 12,000 hr$^{-1}$. Generally the gas space velocity will be on the high side of the range at higher temperatures and will be decreased as the operating temperature decreases.

A number of other oxides and oxide mixtures have been tested for their catalytic activity and have not been found to have useful activity. Silica, for example, has virtually no activity. Iron oxide mixed with phosphorous oxide, selenium oxide or tellurium oxide were also without practical value.

The following non-limiting examples are given by way of illustration only. In the examples the following definitions apply:

$$\text{yield based on the phenol in the feed (\%)} = \frac{\text{desired product (mol/hr)}}{\text{the phenol in the feed (mol/hr)}} \times 100$$

$$\text{yield based on the converted phenol (\%)} = \frac{\text{desired product (mol/hr)}}{\text{the phenol in feed (mol/hr)} - \text{the unreacted phenol (mol/hr)}} \times 100$$

$$\text{yield based on converted methanol (\%)} = \frac{\text{desired product (mol/hr)} \times \text{number of methyl groups in desired product}}{\text{the phenol in feed (mol/hr)} - \text{unreacted methanol (mol/hr)}} \times 100$$

The pressure loss represented by ΔP is the differential pressure across the ends of the catalyst layers. It is measured with a manometer.

EXAMPLE 1

Preparation of Catalyst:

Twenty g. of ammonium metavanadate an 5 g. of oxalic acid are dissolved in 40 cc. of pure water and heated over a boiling water bath to dryness. The dried mass is then heated at 550°C. for three hours in an air stream. The resultant material is ground to 16 – 32 mesh particles and used as the catalyst. Reaction:

A mixture of methanol and phenol in the molar proportion 5 : 1 and nitrogen gas are continuously supplied at a rate 7.9 cc/hr. and 17.7 cc/min. respectively through a preheater maintained at 220°C. in which the feed is vaporized, to a pyrex glass reactor having a 1.8 cm internal diameter containing 1.2 cc. of the catalyst. The reactor is uniformly maintained at 350°C. The reaction is carried out for 50 hours with the gas space velocity of the feed controlled at 9,000 hrs. The resultant product is gas - liquid separated by means of air-cooled traps and dry-ice traps (−78°C.). Gas and liquid are individually analyzed with gas chromatography. According to the analysis, the conversion of phenol was 50.5 percent and the yield of o-cresol and 2,6-xylenol were 62.1 and 28.4 percent respectively based on the phenol converted.

Similar results are obtained with o-cresol and with 2,3-xylenol.

EXAMPLES 2-6

Preparation of Catalyst:

15.6 g. of vanadium trichloride are dissolved in a 100 cc. of pure water. The solution is then agitated, and 24 cc. of 14 percent aqueous ammonia is added dropwise until pH of the solution increases to 6.8. The precipitate formed is washed with water, filtered and then dried for 24 hours at 100°C. The resultant mass is heated for three hours at 650°C. and used as the catalyst.

REACTIONS:

Five runs are made as according to Example 1, using 1.2 cc. of thus prepared catalyst on the feed having molar ratio of methanol to phenol of 3 : 1, and 5 : 1 and that of methanol to phenol to water of 3 : 1 : 3, 3 : 1 : 5 and 5 : 1 : 3, respectively. The results are shown in Table 1. In Table 1, $\Delta P$ is the differential pressue across the catalyst layer. An increase of $\Delta P$ is to be avoided to ensure continued operation. It is observed that the water added effectively inhibited the catalyst particles from breaking into pieces.

EXAMPLES 7-8

Example 1 is repeated to methylate o-cresol with methanol except that the molar ratio of methanol to o-cresol and methanol to o-cresol to water in each feed is 3 : 1 and 3 : 1 : 3, respectively. The results are shown in Table 2.

EXAMPLE 9

Preparation of Catalyst:

In 100 cc. of pure water, there are dissolved 2.9 g. of ammonium metavanadate, 2 g. of oxalic acid and 10.0 g. ferric nitrate represented by $Fe(NO_3)_3 \cdot 9H_2O$. The solution is added with stirring to 378 g. of ALUMINA-SOL (Trademark; manufactured by Nissan Kagaku Kogyo K.K.) containing 10 percent by weight of aluminum oxide, to which is then added dropwise 13 cc. of aqueous ammonia until the pH of the solution increases to 6.8. The precipitate which forms is washed with water, filtered, dried at 110°C. for 24 hours and heated at 450°C. for three hours. The resultant particles are pulverized to the size of 16–32 mesh and used as the catalyst. The atomic ratio of iron to vanadium in the thus prepared catalyst is 2:1, the total amount of vanadium pentoxide and ferric oxide as carried on aluminum oxide being 10 percent by weight based on aluminum oxide. Reaction:

Repetition of Example 1 using 5 cc. of the catalyst prepared as above gave 78.4 percent of converted phenol and the yields of o-cresol and 2,6-xylenol are 72.6 and 24.2 percent, respectively, based on the converted phenol. Similar results are obtained with p-cresol and 3,4,5-trimethylphenol.

EXAMPLES 10-16

Preparation of Catalyst:

One hundred g. of ferric nitrate ($Fe(NO_3)_3 \cdot 9H_2O$) is dissolved in 200 cc. of pure water and 94 cc. of 14 percent aqueous ammonia added to the solution so that the pH of the solution increases to 6.8. The precipitate which forms is washed with water and filtered. Twenty-five g. of the precipitate is added to 50 cc. of an aqueous solution containing 7.2 g. of ammonium metavanadate and 1 g. of oxalic acid dissolved therein. The resultant solution is concentrated to dryness over a boiling water bath. The dried mass is sieved to give 16–32 mesh particles, which are then heated at 450°C. for three hours while air is passed over them to give the catalyst. The atomic ratio of iron to vanadium of the catalyst is 1 : 1. Other catalysts having various atomic ratios are prepared in the same manner.

REACTION:

Example 1 is repeated using seven different catalysts prepared in accordance with the example. The results are shown in Table 3.

EXAMPLE 17-20

Preparation of Catalyst:

One hundred grams of ferric nitrate is dissolved in 200 cc. of pure water, and 94 cc. of 14 percent aqueous ammonia added dropwise to the resultant solution until the pH of the solution reaches 6.8. The precipitate which forms is washed with water and filtered. Twenty five g. of the thus obtained precipitate is added to 50 cc. of an aqueous solution of ammonium metavanadate. The resultant solution is concentrated to dryness over a hot water bath. The dried mass is sieved to give 16–32 mesh particles, which are heated at 650 °C. for three hours under passing air to give the catalyst. The atomic ratio of iron to vanadium in the catalyst is 1 : 1. Other catalysts of various atomic ratios are prepared in the similar manner.

REACTION:

Six runs are made in accordance with Example 1 except that the compositions of feeds are varied. Example 17 is run on a mixture of methanol with phenol in the molar ratio of 5 : 1, while Examples 18–22, are run on a mixture of methanol, phenol and water in the molar ratio of 5 : 1 : 3, respectively. The results measured after passage of 100 reaction hours are shown in Table 4.

EXAMPLE 23

Preparation of Catalyst:

In 100 cc. of pure water, there are dissolved 7.8 g. of vanadium trichloride and 10.0 g. of ferric nitrate. Then, 18 cc. of 14 percent aqueous ammonia are added dropwise to the resultant solution until the pH of the solution increases to 6.8. The precipitate formed is then washed with water, filtered and dried at 110°C. for 24 hours. The dried material is heated at 650°C. for three hours in the air stream to give ghe catalyst. The atomic ratio of iron to vanadium of the catalyst is 0.5 : 1.

REACTION:

The reaction is carried out on a mixed feed of methanol, phenol and water in the molar proportion of 8 : 1 : 6, using 2 cc. of the catalyst. The mixture feed is supplied to the reactor at a rate of 7.9 cc./hr. The procedure is similar to Example 1, but the nitrogen carrier gas is omitted. A comparative test is run by repeating the same procedure except that the water is replaced by nitrogen in the same mol fraction. The result obtained after the passage of 48 hours is shown in Table 5.

EXAMPLES 24–34

Preparation of Catalyst:

In 200 cc. of pure water are dissolved 21.4 g. of ammonium metavanadate and 34.4 g. of ferrous sulfate ($FeSO_4 \cdot 7H_2O$). The resultant solution is added, all at one time, with stirring to 86 cc. of 14 percent aqueous ammonia with stirring to form a precipitate. The precipitate is washed with water, filtered, dried for 24 hours at 110°C. and further heated another three hours at 650°C. in the air stream to give the catalyst. The atomic ratio of iron to vanadium of the catalyst is 1 : 1.

REACTION:

Example 1 is repeated using 2 cc. of catalyst for each run on the feed of various compositions. The feed is supplied at a rate of 7.9 cc./hr. at a room temperature.

The results obtained after the passage of 100 hours are shown in Table 6.

EXAMPLE 35

Preparation of Catalyst:

An aqueous solution prepared by dissolving 69.1 g. of ferric nitrate in 150 cc. of pure water is added with stirring to an aqueous solution of 20.0 g. of ammonium metavanadate and 6 g. of oxalic acid dissolved in 150 cc. of pure water. To the resultant solution there is added dropwise 55 cc. of 14 percent aqueous ammonia until the pH of the solution increases to 6.8. The precipitate which forms is washed with water, filtered, dried for 24 hours at 110°C. and further heated for another three hours in an air stream, to give the catalyst. The atomic ratio of iron to vanadium of the catalyst is 1 : 1.

REACTION:

Example 1 is repeated for 600 hours on a feed mixture of methanol, phenol and water in the molar ratio of 8 : 1 : 6. The changes measured with the passage of reaction times are shown in Table 7.

EXAMPLE 36

Methylation of o-cresol with methanol is made in the presence of the catalyst as in Example 13 having an atomic ratio of iron to vanadium of 1:1. Example 1 is repeated on the feed of which molar ratio of phenol to o-cresol is 3 : 1, to give o-cresol conversion of 95.8 percent and a yield of 2,6-xylenol based on converted o-cresol of 97.5 percent. Similar results are obtained when the nitrogen is replaced with methane.

EXAMPLE 37

O-cresol is methylated with methanol, using the catalyst as prepared in Example 24. Example 1 is repeated on a feed containing methanol, o-cresol and water in the proportion of 3 : 1 : 3. After 100 hours, ΔP reaches 9.5 cm $H_2O$, o-cresol conversion is 85.8 percent and the yield of 2,6-xylenol is 83.4 percent.

EXAMPLE 38

Methylation of phenol and o-cresol with methanol is made using the catalyst as prepared in Example 13. Example 1 is repeated except that the molar ratio of methanol to phenol is 4 : 1 and phenol to O-cresol is 2 : 1. An analysis of product liquid shows 12.4 percent of phenol, 24.1 percent of o-cresol and 61.4 percent of 2,6-xylenol.

EXAMPLE 39

A mixture of phenol and o-cresol is subjected to methylation reaction with methanol according to Example 1 except that the proportion of methanol, phenol, o-cresol and water in the feed is 4 : 1 : 2 : 6 using 2 cc. of the catalyst are prepared in the catalyst. After the passage of 96 reaction hours, P reaches 4.3 cm $H_2O$. The composition of the product liquid as analyzed by a gas chromatography is 4.2 percent of phenol, 15.7 percent of o-cresol and 79.3 percent of 2,6-xylenol.

EXAMPLES 40–47

Preparation of Catalyst:

In 130 cc. of water there are dissolved 25.0 g. of ferric nitrate ($Fe(NO_3)_3 \cdot 9H_2O$), 7.2 g. of ammonium metavanadate and 5 g. of oxalic acid. To the resultant solution there are added 20 cc. of an aqueous solution of 1.59 g. of magnesium nitrate ($Mg(NO_3)_2 \cdot 6H_2O$). The pH of the solution is increased to 6.8 by adding 32 cc. of 14 percent aqueous ammonia with stirring. The precipitate which forms is washed with water, filtered, dried at 110°C. for 24 hours and heated at 450°C. for another 3 hours. The atomic ratio of iron to vanadium of the catalyst is 1, magnesium to iron is 0.1 : 1. Another catalyst containing titanium oxide is prepared by repeating the above operation with titanium tetrachloride substituted for magnesium nitrate. Another catalyst containing magnesium oxide and titanium oxide is prepared in a similar manner by adding magnesium nitrate and titanium tetrachloride.

REACTION:

Example 1 is repeated using catalysts as tabulated in Table 8.

EXAMPLE 48–54

Preparation of Catalyst:

In 150 cc. water there are dissolved 25.0 g. ferric nitrate, 7.2 g. of ammonium metavanadate, 5 g. oxalic acid and 4.67 g. of manganese nitrate ($Mn(NO_3)_2 \cdot 4H_2O$). With stirriing, 36 cc. of 14 percent aqueous ammonia is added dropwise until the pH of the solution increases to 6.8. The precipiptate formed is washed with water, filtered, dried at 110°C. for 24 hours, and heated at 450°C. for another three hours, to give the catalyst. The atomic ratio of iron to vanadium of thus prepared catalyst is 1, and that of manganese to iron is 0.3 : 1. In similar manner, a number of catalysts having different composition are prepared.

REACTION:

Seven runs are made in accordance with Example 1 using seven different catalysts and the results are tabulated in Table 9.

EXAMPLES 55–68

Preparation of Catalyst:

In 130 cc. of water there are dissolved 25.0 g. ferric nitrate, 7.2 g. ammonium metavanadate and 5 g. oxalic acid. To the resultant solution is then added 30 cc. of an aqueous solution containing 1.59 g. magnesium nitrate, 1.17 g. titanium tetrachloride and 4.67 g. manganese nitrate. With agitation, 41 cc. of 14 percent aqueous ammonia are added dropwise to the resultant mixture solution until the pH reaches 6.8. The precipitate formed is washed with water, filtered, dried at 110°C. for 24 hours and heated at 450°C. for three hours, to give the catalyst. The various atomic ratios in the catalyst are as follows:

Fe/V = 1, Mg/Fe = 0.1, Ti/Fe = 0.1 and Mn/Fe = 0.1.

In a similar manner an additional 13 catalysts of different compositions are prepared.

REACTION:

In each run, Example 1 is repeated using the catalyst prepared as above. Results are shown in Table 10.

EXAMPLE 69

Methylation is carried out for 1800 hours in succession using the catalyst as prepared in Example 62. The composition of the catalyst is such that Fe/V = 1, Mg/Fe = Ti/Fe = 0.1, Mn/Fe = 0.3. Example 1 is repeated using 5 cc. of the catalyst on the feed having a methanol, phenol, water ratio of 8 : 1 : 6. Results are shown in Table 11.

EXAMPLE 70

Preparation of Catalyst:

In 150 cc. of water are dissolved 25.0 g. ferric nitrate, 7.2 g. ammonium metavanadate, 5 g. oxalic acid and 3.47 g. beryllium nitrate. With titration, 35 cc. of 14 percent aqueous ammonium are added dropwise to the resultant solution until the pH of the solution increases to 6.8. The precipitate formed is washed with water, filtered, dried at 110°C. for 24 hours and heated at 450°C. for three hours to give the catalyst. The atomic ratio of iron to vanadium is 1 : 1 and that of beryllium to iron is 0.3 : 1.

REACTION:

Repetition of Example 1 using thus prepared catalyst gives, after 100 hours, 79.8 percent phenol conversion and 40.0 percent yield of 2,6-xylenol based on phenol in the feed.

EXAMPLE 71

Preparation of Catalyst:

Twenty five g. of ferric nitrate, 47.2 g. of ammonium metavanadate, and 5 g. of oxalic acid are dissolved in 150 cc. of water. To the resultant solution is added dropwise with stirring, 24 cc. of 14 percent aqueous ammonia until the pH of the solution reaches 6.8. The precipitate formed is washed with water, filtered, a solid lump is obtained. The lump is suspended in 50 cc. of water, to which 1.15 g. boric acid is added and the whole dried over a boiling water bath, dried at 110°C. for 24 hours and heated at 450°C. for three hours. The atomic ratio of iron to vanadium is 1 : 1, that of boron to iron being 0.3 : 1.

REACTION:

Example 1 is repeated using the thus prepared catalyst, giving 81.2 percent phenol conversion. The yield of 2,6-xylenol based on phenol in the feed is 39.6 percent and the total yield of o-cresol plus 2,6-xylenol based on converted methanol is 49.6 percent.

EXAMPLE 72

Methylation of o-cresol with methanol is made in accordance with Example 1 using the same catalyst as prepared in Example 64 on a feed material containing methanol, o-cresol and water in a molar proportion of 3 : 1 : 3. One hundred and twenty hours of reaction gives 88.9 percent o-cresol conversion. The yield of 2,6-xylenol based on o-cresol in the feed material is 87.4 percent.

EXAMPLE 73

A mixture of phenol and o-cresol is methylated with methanol using 2cc. of the same catalyst as prepared in Example 64, in accordance with Example 1 on a feed containing methanol, phenol, o-cresol and water in a molar proportion of 4:1:2:6. After 100 hours, $\Delta P$ reaches 3.6 cm $H_2 O$. The composition of the liquid product as analyzed by a gas chromatography is 2.5 percent phenol, 13.9 percent o-cresol and 82.2 percent of 2,6-xylenol.

EXAMPLE 74

Preparation of Catalyst:

To 150 cc. of an aqueous solution of 10 percent oxalic acid is added 27 g. vanadium pentoxide, which is then dissolved by heating the mixture at 80°C. The solution is concentrated to dryness over a boiling water bath and heated at 500°C. for 3 hours under passing air, giving vanadium oxide which is used as the catalyst. Repetition of the experiment of Example 1 using this catalyst gives, after 48 hours of reaction, 45.8 percent phenol conversion. The yields of o-cresol and 2,6-xylenol based on converted phenol are 63.3 percent and 27.9 percent respectively. Similar results are obtained with 2-xylylphenol and 2-tolyl-4-phenylphenol.

EXAMPLE 75

Preparation of Catalyst:

To 150 cc. of a 10 percent oxalic acid aqueous solution is added 18 g. of vanadium pentoxide and 15.8 g. of ferric nitrate, which are then heated for dissolving. The resultant solution is concentrated to dryness over a boiling water bath. The dried material is heated at 500°C. for three hours under passing air to give vanadium oxide catalyst. The atomic ratio of iron to vanadium of the catalyst is 1 : 1.

REACTION:

Example 1 is repeated using the thus prepared catalyst to give, after 50 hours, 65.4 percent phenol conversion. The yields of o-cresol based on converted phenol and that of 2,6-xylenol based on converted phenol are 66.8 percent and 30.2 percent, respectively.

Table 1

| Example No. | Feed Composition (mole) | | | Reaction Time (hr.) | $\Delta P$ (cm $H_2O$) | Phenol Conversion (%) | Yield Based on Phenol in Feed | |
|---|---|---|---|---|---|---|---|---|
| | methanol | ethanol | water | | | | o-Cresol | 2,6-Xylenol |
| 2 | 3 | 1 | — | 100 | 10.25 | 27.1 | 21.3 | 4.1 |
| 3 | 3 | 1 | 3 | 97 | 20.1 | 28.3 | 20.7 | 5.3 |
| 4 | 3 | 1 | 5 | 102 | 7.2 | 34.9 | 23.8 | 8.4 |
| 5 | 5 | 1 | — | 101 | 84.6 | 45.7 | 29.0 | 13.1 |
| 6 | 5 | 1 | 3 | 100 | 13.3 | 48.2 | 27.9 | 15.6 |

Table 2

| Example No. | Feed Composition (mole) methanol | o-cresol | water | Reaction Time (hr.) | ΔP (cmH₂O) | o-Cresol Conversion (%) | Yield of 2,6-Xylene Based on o-Cresol in Feed (%) |
|---|---|---|---|---|---|---|---|
| 7 | 3 | 1 | — | 100 | 99.2 | 55.2 | 51.3 |
| 8 | 3 | 1 | 3 | 100 | 12.0 | 58.6 | 53.3 |

Table 3

| Example No. | Atomic ratio of Catalyst V/Fe | Phenol Conversion (%) | Yield Based on Phenol in Feed (%) o-Cresol | 2,6-Xylenol | Yield of o-Cresol and 2,6-Xylenol (%) Based on Converted Phenol | Based on Converted Methanol |
|---|---|---|---|---|---|---|
| 10 | 1/9 | 48.8 | 27.5 | 14.5 | 86.2 | 28.8 |
| 11 | 1/4 | 71.8 | 38.7 | 31.4 | 97.7 | 34.8 |
| 12 | 1/2 | 89.4 | 52.6 | 34.8 | 98.9 | 35.4 |
| 13 | 1/1 | 91.5 | 47.2 | 39.7 | 97.4 | 41.6 |
| 14 | 2/1 | 73.9 | 38.9 | 32.4 | 98.2 | 38.4 |
| 15 | 4/1 | 70.4 | 37.1 | 32.0 | 98.1 | 40.3 |
| 16 | 9/1 | 64.2 | 35.8 | 20.2 | 93.4 | 29.2 |
| Comparative Test | Fe | 9.2 | 7.0 | 0.7 | 83.4 | 13.4 |

Table 4

| Example No. | Atomic ratio of Catalyst (V/Fe) | Water | ΔP (cm H₂O) | Phenol Conversion (%) | Yield Based on Phenol in Feed (%) o-Cresol | 2,6-Xylenol | Total Yield of o-Cresol and 2,6-Xylenol Based on Converted Phenol (%) |
|---|---|---|---|---|---|---|---|
| 17 | 1/1 | — | 72.8 | 89.9 | 47.5 | 40.8 | 98.2 |
| 18 | 1/9 | Added | 4.3 | 67.3 | 37.3 | 21.9 | 88.1 |
| 19 | 1/2 | — Do | 6.0 | 90.2 | 51.7 | 37.1 | 98.6 |
| 20 | 1/1 | — Do | 6.4 | 93.8 | 45.4 | 46.5 | 98.0 |
| 21 | 2/1 | — Do | 7.8 | 77.4 | 38.8 | 37.2 | 98.2 |
| 22 | 9/1 | — Do | 16.7 | 71.8 | 39.6 | 27.0 | 92.7 |

Table 5

| Example No. | Feed Composition (Molar Ratio) Methanol | Phenol | Water | Nitrogen | ΔP (cm H₂O) | Phenol Conversion (%) | Yield Based on Phenol in Feed (%) o-Cresol | 2,6-Xylenol |
|---|---|---|---|---|---|---|---|---|
| 23 | 8 | 1 | 6 | — | 4.1 | 99.0 | 8.8 | 85.9 |
| Comparative Test | 8 | 1 | — | 6 | 53.6 | 88.2 | 23.4 | 64.0 |

Table 6

| Example No. | Feed Composition (Molar Ratio) Methanol | Phenol | Water | P (cm H₂O) | Phenol Conversion (%) | Yield Based on Phenol in Feed (%) o-Cresol | 2,6-Xylenol |
|---|---|---|---|---|---|---|---|
| 24 | 8 | 1 | — | 63.7 | 66.6 | 40.7 | 25.4 |
| 25 | 5 | 1 | — | 79.4 | 40.1 | 32.9 | 7.1 |
| 26 | 2 | 1 | — | 103.8 | 10.5 | 10.0 | 0.4 |
| 27 | 8 | 1 | 2.1 | 10.7 | 90.4 | 27.2 | 62.2 |
| 28 | 8 | 1 | 3 | 5.6 | 93.5 | 14.6 | 78.0 |
| 29 | 8 | 1 | 6 | 4.3 | 94.4 | 15.8 | 77.4 |
| 30 | 8 | 1 | 12 | 4.0 | 97.0 | 12.4 | 80.6 |
| 31 | 5 | 1 | 3 | 7.2 | 78.6 | 42.4 | 35.6 |
| 32 | 5 | 1 | 6 | 5.4 | 87.1 | 40.5 | 45.6 |
| 33 | 2 | 1 | 3 | 18.8 | 22.3 | 18.0 | 4.2 |
| 34 | 2 | 1 | 6 | 11.2 | 29.8 | 22.3 | 7.2 |

Table 7

| Example No. | Reaction Time (hr.) | P (cm H$_2$O) | Phenol Conversion (%) | Yield Based on Phenol in Feed (%) | |
|---|---|---|---|---|---|
| | | | | o-Cresol | 2,6 Xylenol |
| 35 | 18 | 6.2 | 88.4 | 28.5 | 58.6 |
| | 114 | 6.5 | 88.1 | 29.6 | 57.6 |
| | 210 | 6.7 | 83.1 | 34.0 | 48.3 |
| | 285 | 6.6 | 86.0 | 26.6 | 58.0 |
| | 361 | 6.9 | 89.4 | 26.4 | 61.8 |
| | 456 | 7.1 | 90.7 | 25.9 | 63.7 |
| | 504 | 7.1 | 90.2 | 30.0 | 59.3 |
| | 601 | 7.3 | 88.6 | 31.1 | 56.3 |

Table 8

| Example No. | Composition of Catalyst in Atomic Ratio | Reaction Time (hr.) | Phenol Conversion(%) | yield Based on Phenol in Feed (%) | | Total Yield of o-Cresol and 2,6-Xylenol | |
|---|---|---|---|---|---|---|---|
| | | | | o-Cresol | 2,6-Xylenol | Based on Converted Phenol | Based on Converted Methanol |
| 40 | V$_1$Fe$_1$Mg$_{0.1}$ | 1 | 97.4 | 23.0 | 72.1 | 97.7 | 40.1 |
| | | 5 | 90.2 | 25.8 | 62.8 | 98.2 | 38.8 |
| | | 50 | 89.8 | 28.1 | 60.3 | 98.5 | 37.9 |
| 41 | V$_1$Fe$_1$Mg$_{0.3}$ | 5 | 86.1 | 26.2 | 58.5 | 98.3 | 36.2 |
| | | 48 | 85.3 | 32.1 | 52.2 | 98.8 | 34.6 |
| 42 | V$_1$Fe$_2$Mg$_{0.1}$ | 5 | 88.5 | 29.2 | 57.9 | 98.4 | 38.4 |
| | | 46 | 86.9 | 29.9 | 55.7 | 98.5 | 37.9 |
| 43 | V$_2$Fe$_1$Mg$_{0.1}$ | 5 | 95.8 | 13.9 | 76.7 | 94.6 | 31.0 |
| | | 50 | 81.1 | 41.7 | 38.4 | 98.7 | 29.8 |
| 44 | V$_1$Fe$_1$Ti$_{0.1}$ | 1 | 96.9 | 33.9 | 60.9 | 97.9 | 38.4 |
| | | 5 | 90.6 | 35.6 | 53.7 | 98.6 | 37.2 |
| | | 50 | 88.8 | 36.4 | 51.1 | 98.6 | 36.9 |
| 45 | V$_1$Fe$_1$Ti$_{0.3}$ | 5 | 85.4 | 33.7 | 50.3 | 98.4 | 36.1 |
| | | 50 | 81.6 | 37.5 | 43.0 | 98.7 | 33.3 |
| 46 | V$_1$Fe$_1$Mg$_{0.1}$Tk$_{0.05}$ | 1 | 96.8 | 25.8 | 69.0 | 97.9 | 40.7 |
| | | 5 | 87.2 | 27.1 | 58.6 | 98.3 | 40.0 |
| | | 50 | 86.5 | 27.8 | 57.4 | 98.5 | 38.7 |
| 47 | V$_1$Fe$_1$Mg$_{0.05}$Ti$_{0.1}$ | 1 | 96.4 | 32.5 | 62.0 | 98.0 | 39.4 |
| | | 5 | 89.5 | 33.2 | 54.7 | 98.2 | 38.2 |
| | | 50 | 87.8 | 34.1 | 52.3 | 98.5 | 37.6 |

Table 9

| Example No. | Composition of Catalyst (Atomic Ratio) | Phenol Conversion (%) | Yield Based on Phenol in Feed (%) | | Total Yield of o-Cresol and 2,6-Xylenol (%) | |
|---|---|---|---|---|---|---|
| | | | o-Cresol | 2,6-Xylenol | Based on Converted Phenol | Based on Converted Methanol |
| 48 | V$_1$Fe$_1$Mn$_{0.1}$ | 94.0 | 25.4 | 66.1 | 97.3 | 49.8 |
| 49 | V$_1$Fe$_1$Mn$_{0.3}$ | 93.8 | 25.8 | 65.5 | 97.3 | 50.6 |
| 50 | V$_1$Fe$_1$Mn$_{0.5}$ | 89.7 | 27.2 | 60.3 | 97.5 | 51.1 |
| 51 | V$_1$Fe$_1$Mn$_{0.7}$ | 84.1 | 30.1 | 52.4 | 98.1 | 49.7 |
| 52 | V$_1$Fe$_1$Mn$_{1.0}$ | 80.9 | 36.4 | 44.0 | 98.4 | 48.3 |
| 53 | V$_1$Fe$_2$Mn$_{0.3}$ | 90.6 | 30.8 | 57.4 | 97.4 | 48.9 |
| 54 | V$_2$Fe$_1$Mn$_{0.3}$ | 96.2 | 16.9 | 73.8 | 94.4 | 42.2 |

Table 10

| Example No. | Composition of Catalyst (Atomic Ratio) V:Fe: Mg:Ti:Mn | Phenol Conversion | Yield Based on Phenol in Feed (%) | | Total Yield of o-Cresol and 2,6-Xylenol (%) | |
|---|---|---|---|---|---|---|
| | | | o-Cresol | 2,6-Xylenol | Based on Converted Phenol | Based on Converted Methanol |
| 55 | 1:1:0.1:0:0.3 | 86.6 | 39.0 | 45.8 | 97.9 | 50.9 |
| 56 | 1:1:0.1:0:0.5 | 81.4 | 37.5 | 42.5 | 98.2 | 48.2 |
| 57 | 1:1:0.3:0:0.3 | 82.6 | 36.8 | 43.6 | 97.3 | 44.5 |
| 58 | 1:1:0.3:0:0.5 | 78.3 | 36.0 | 40.8 | 98.1 | 47.1 |
| 59 | 1:1:0:0.1:0.3 | 86.0 | 35.8 | 49.2 | 98.8 | 50.7 |
| 60 | 1:1:0:0.1:0.5 | 84.3 | 37.7 | 45.6 | 98.8 | 48.2 |
| 61 | 1:1:0.1:0.1:0 | 87.9 | 35.4 | 50.4 | 97.6 | 36.4 |
| 62 | 1:1:0.3:0.1:0.5 | 76.5 | 37.5 | 38.1 | 98.9 | 46.3 |
| 63 | 1:1:0.1:0.1:0.1 | 87.3 | 25.8 | 60.2 | 98.5 | 49.0 |
| 64 | 1:1:0.1:0.1:0.3 | 89.9 | 26.1 | 62.4 | 98.4 | 51.2 |
| 65 | 1:1:0.1:0.1:0.5 | 88.3 | 28.5 | 58.1 | 98.1 | 50.6 |
| 66 | 1:1:0.1:0.1:0.7 | 80.8 | 29.5 | 50.2 | 98.6 | 50.8 |
| 67 | 1:2:0.1:0.1:0.3 | 86.5 | 28.0 | 56.5 | 97.7 | 47.7 |
| 68 | 2:1:0.1:0.1:0.3 | 93.2 | 19.7 | 70.1 | 96.3 | 41.3 |

Table 11

| Example No. | Reaction Time (hr.) | ΔP (cm H₂O) | Phenol Conversion (%) | Yield Based on Phenol in Feed (%) o-Cresol | 2,6-Xylenol |
| --- | --- | --- | --- | --- | --- |
|    | 100  | 5.3 | 82.6 | 29.4 | 51.6 |
|    | 302  | 5.3 | 80.1 | 30.8 | 48.7 |
|    | 506  | 5.6 | 83.0 | 30.2 | 51.2 |
|    | 750  | 5.4 | 82.7 | 31.1 | 49.9 |
| 69 | 1002 | 5.9 | 78.8 | 30.3 | 47.3 |
|    | 1455 | 6.2 | 79.4 | 29.6 | 48.4 |
|    | 1806 | 6.2 | 76.7 | 29.5 | 45.9 |

What is claimed is:

1. A metallic oxide catalyst comprising an oxide or iron, an oxide of vanadium, and at least one oxide selected from the group consisting of oxides of manganese, magnesium, titanium, beryllium and boron in which the atomic ratio of iron to vanadium to other metal or mixture thereof is from about 9 to 1/9 : 1 : 1 − 0.01.

2. A catalyst as in claim 1 wherein said other oxide is manganese oxide.

3. A catalyst as in claim 1 wherein said other oxide is magnesium oxide.

4. A catalyst as in claim 1 wherein said other oxide is titanium oxide.

5. A catalyst as in claim 1 containing oxides of vanadium, iron, magnesium, titanium and manganese.

* * * * *

UNITED STATES PATENT OFFICE
CERTIFICATE OF CORRECTION

PATENT NO. : 3,937,669

DATED : February 10, 1976

INVENTOR(S) : HITOSHI NAKAJIMA ET AL.

It is certified that error appears in the above-identified patent and that said Letters Patent are hereby corrected as shown below:

Claim 1, line 1, change "or" to read -- of --.

Signed and Sealed this eleventh Day of May 1976

[SEAL]

Attest:

RUTH C. MASON
Attesting Officer

C. MARSHALL DANN
Commissioner of Patents and Trademarks